United States Patent
Zheng et al.

(10) Patent No.: US 9,110,035 B2
(45) Date of Patent: Aug. 18, 2015

(54) METHOD AND SYSTEM FOR DETECTING DEFECTS OF TRANSPARENT SUBSTRATE

(75) Inventors: Yuan Zheng, Shanghai (CN); Jean-Philippe Schweitzer, Shanghai (CN); Xiaofeng Lin, Shanghai (CN); Dazhi Chen, Shanghai (CN)

(73) Assignee: SAINT-GOBAIN GLASS FRANCE, Courbevoie (FR)

( * ) Notice: Subject to any disclaimer, the term of this patent is extended or adjusted under 35 U.S.C. 154(b) by 352 days.

(21) Appl. No.: 13/266,308

(22) PCT Filed: May 14, 2010

(86) PCT No.: PCT/CN2010/072782
§ 371 (c)(1),
(2), (4) Date: Oct. 26, 2011

(87) PCT Pub. No.: WO2010/130226
PCT Pub. Date: Nov. 18, 2010

(65) Prior Publication Data
US 2012/0044344 A1 Feb. 23, 2012

(30) Foreign Application Priority Data

May 15, 2009 (CN) .......................... 2009 1 0139054

(51) Int. Cl.
*H04N 7/18* (2006.01)
*G01N 21/896* (2006.01)
(Continued)

(52) U.S. Cl.
CPC .............. *G01N 21/896* (2013.01); *G01N 21/88* (2013.01); *G06K 9/00* (2013.01); *H04N 7/18* (2013.01); *G01N 2021/8825* (2013.01)

(58) Field of Classification Search
CPC ....................................................... H04N 7/18
USPC ........................................................ 348/93
See application file for complete search history.

(56) References Cited

U.S. PATENT DOCUMENTS 5,943,550 A * 8/1999 Fulford et al. ................... 438/14
6,426,501 B1 * 7/2002 Nakagawa ........................ 850/5
(Continued)

FOREIGN PATENT DOCUMENTS

CN 1633582 A 6/2005
CN 101346624 A 1/2009
WO WO 2007/045437 4/2007

OTHER PUBLICATIONS

International Search Report as issued for International Patent Application No. PCT/CN2010/072782, dated Aug. 26, 2010.

*Primary Examiner* — Richard Torrente
*Assistant Examiner* — Irfan Habib
(74) *Attorney, Agent, or Firm* — Pillsbury Winthrop Shaw Pittman LLP

(57) ABSTRACT

A method and a system for detecting defects of a transparent substrate are provided. The system includes: a plurality of detection channels, each of which includes an illumination component for providing illumination to the substrate and an imaging component for scanning the substrate to provide image of the substrate; a transport module, for producing relative motion between the substrate and the illumination components and the imaging components included in the plurality of detection channels; and a controlling module, for controlling the illumination components and the imaging components included in the plurality of detection channels so that at least two illumination components of the illumination components included in the plurality of detection channels provide illumination to the substrate alternately, and the imaging component included in any of the plurality of detection channels scans the substrate when the illumination component included in that detection channel illuminates the substrate, wherein the imaging components included in at least two detection channels of the plurality of detections channels are the same imaging component. The method and system described by the present invention is capable of discriminating real defects from fake defects which enables substrate to be inspected with free of cleaning.

38 Claims, 8 Drawing Sheets

(51) Int. Cl.
  *G01N 21/88*  (2006.01)
  *G06K 9/00*  (2006.01)

(56) References Cited

U.S. PATENT DOCUMENTS

| | | | |
|---|---|---|---|
| 6,437,357 B1* | 8/2002 | Weiss et al. | 250/559.4 |
| 6,894,271 B2* | 5/2005 | Widzgowski | 250/234 |
| 7,256,881 B2 | 8/2007 | Leppard et al. | |
| 2002/0167723 A1* | 11/2002 | Eda et al. | 359/368 |
| 2004/0207836 A1* | 10/2004 | Chhibber et al. | 356/237.4 |
| 2004/0218262 A1* | 11/2004 | Chuang et al. | 359/366 |
| 2005/0163398 A1* | 7/2005 | Ioka | 382/284 |
| 2006/0133657 A1* | 6/2006 | Schmid et al. | 382/128 |
| 2007/0229809 A1* | 10/2007 | Belyaev et al. | 356/237.2 |
| 2007/0263206 A1* | 11/2007 | LeBlanc et al. | 356/239.7 |
| 2007/0286473 A1* | 12/2007 | Leslie et al. | 382/146 |
| 2008/0055593 A1* | 3/2008 | Fox | 356/244 |
| 2008/0198602 A1 | 8/2008 | Brittain et al. | |
| 2009/0128648 A1* | 5/2009 | Ikeda et al. | 348/222.1 |
| 2011/0304725 A1* | 12/2011 | Sakai et al. | 348/92 |
| 2011/0320149 A1* | 12/2011 | Lee et al. | 702/83 |
| 2014/0072203 A1* | 3/2014 | Wu et al. | 382/149 |

* cited by examiner

METHOD AND SYSTEM FOR DETECTING DEFECTS OF TRANSPARENT SUBSTRATE

CROSS-REFERENCE TO RELATED APPLICATIONS

The present application is the U.S. National Stage of PCT/CN2010/072782, filed May 14, 2010, which in turn claims a priority to Chinese patent application No. 200910139054.5 filed on May 15, 2009. The content of all of the applications are incorporated herein by reference in their entirety.

FIELD OF THE INVENTION

The present invention generally relates to a method and system for detecting local defects of a substrate, and, more specifically, relates to an optical method and system for detecting local defects both within and on surface(s) of a transparent substrate.

BACKGROUND OF THE INVENTION

Defects inspection is very important in terms of quality control of substrate manufacturing. For example, In the filed of glass manufacture, various types of defects such as scratches, stains, tin pick-ups, chips in terms of surface defects, and bubbles, stones, knots in terms of internal defects, may be formed in glass substrate during the process of manufacturing. Tasks of defect inspection are not only to defects but also to accurately categorize these defects since specifications of quality control are different for various types of defects.

Optical methods are widely applied in defect inspection. In general, there are collimated illumination and diffusive illumination in terms of way of illumination; bright field detection and dark field detection in terms of way of image acquisition; transmission detection and reflection detection in terms of direction of light propagating at surface of inspected object. Different methods need to be applied to characterize different types of defects. For example, collimated illumination is sensitive to deformation or inhomogeneity of refractive index, which can be used to inspect knots or stones. Diffusive illumination is usually used for inspecting core size of defect. Tin pick-up is easy to be inspected under reflection inspection due to high reflectivity. Generally, combination of different methods of inspection is an efficient way to detect and categorize different type of defects.

WO patent application No. 2007/045437 entitled "System and Method for Optically Inspecting Glass Panes" which was published on Apr. 26, 2007 discloses a multi-channel inspection system, where glass panes to be detected passes through three separate inspection modules in series. And each module have respective illumination component, sensing component and image processing component to provide respective inspection of different types of defects. Disadvantages of this system are high cost and large size due to each detection module will have a full set of illumination component, sensing component and image processing component. U.S. patent application No. 2007/0263206 entitled "Apparatus and Method for Characterizing Defects in a Transparent Substrate" which published on Nov. 15, 2007 relates to an inspection system with mixed multiple illumination, where multiple light sources illuminate inspected substrate simultaneously, and the at the same time imaging device captures mixed signals of bright field and dark field. Compared with separated illuminations of each light source, image features of defects under the mixed illumination were reduced because of interference between each illumination. As a result, difficulty of image processing for defects detection and categorization will be increased.

Usually, washing process of substrate is required before inspection of defects since foreign particles such as dust on surface of the substrate may result in misclassification of the particles misclassified as real defects. It will undoubtedly increase fake defects rate of inspection (i.e. the probability of categorizing fake defects as real defects) and consequently increase waste of qualified product. However, a washing machine is typically expensive in terms of cost of the equipment and electric power consumption. On the other hand, washing process sometimes is not feasible or has negative influence on the substrate. One example is inspection of glass ribbon on float line. Another example is glass substrates of flat planes display module, which have a thickness of around 0.7 mm and are likely to break during washing process due to small thickness. A further example is that water mark on the substrate is not acceptable for some applications.

Therefore, there is a need to provide a defect inspection method and defect inspection system which provide high performance to price ratio with compact multi-channel configuration and without interference of multiple illuminations. Beside that, there is further requirement to provide a system and method capable of detecting and categorizing defects of unclean substrate.

SUMMARY OF THE INVENTION

An object of the present invention is to provide an optical method and optical system for inspecting defects of a transparent substrate. The method and system of the present invention is capable of providing images of a plurality of inspection channels by sharing not only an imaging component but also an illumination component. By way of controlling a plurality of illumination components illuminate the substrate alternately, interference of multiple inspection channels is eliminated. The method and system described by the present invention is capable of discriminating real defects from fake defects which enable inspected substrate is free of cleaning.

In first aspect of the present invention, a system for detecting defects of a transparent substrate which comprises: a plurality of detection channels, each of which includes an illumination component for providing illumination to the substrate and an imaging component for scanning the substrate to provide image of the substrate; a transport module, for producing relative motion between the substrate and the illumination components and the imaging components included in the plurality of detection channels; and a controlling module, for controlling the illumination components and the imaging components included in the plurality of detection channels so that at least two illumination components of the illumination components included in the plurality of detection channels provide illumination to the substrate alternately, and the imaging component included in any of the plurality of detection channels scans the substrate when the illumination component included in that detection channel illuminates the substrate, wherein the imaging components included in at least two detection channels of the plurality of detections channels are the same imaging component.

In second aspect of the present invention, a method for detecting defects of transparent substrate comprises steps of: using a plurality of detection channels to provide images of the substrate, wherein each of the plurality of detection channels includes an illumination component for providing illumination to the substrate and an imaging component for scanning the substrate to provide an image of the substrate;

producing relative motion between the substrate and the illumination components and the imaging components included in the plurality of detection channels; and controlling the illumination components and the imaging components included in the plurality of detection channels so that at least two illumination components of the illumination components included in the plurality of detection channels provide illumination to the substrate alternately, and the imaging component included in any of the plurality of detection channels scans the substrate when the illumination component included in that detection channel illuminates the substrate, wherein the imaging components included in at least two detection channels of the plurality of detections channels are the same imaging component.

Defect detection configuration of the present invention is compact and low cost by sharing at least part of illumination component and imaging components with a plurality of different inspection channel. Furthermore, since illumination component work in a pulse mode which facilitates heat dissipation, the illumination component may have a long lifetime and provide higher brightness. (In addition, since inspection zone of multiple inspection channels is confined in narrow strip, influence of substrate flattering during conveying of substrate is significantly reduced.) Moreover, in the present invention, by way of controlling a plurality of illumination components to illuminate the substrate alternately via trigger controlling, interference of multiple inspection channels is eliminated.

BRIEF DESCRIPTION OF THE DRAWINGS

The above and the other features of the present invention will be understood better from the following detailed description of exemplified embodiments of the present invention with reference to the accompanying drawings.

DETAILED DESCRIPTION OF THE PREFERRED EMBODIMENTS

Figure 1:
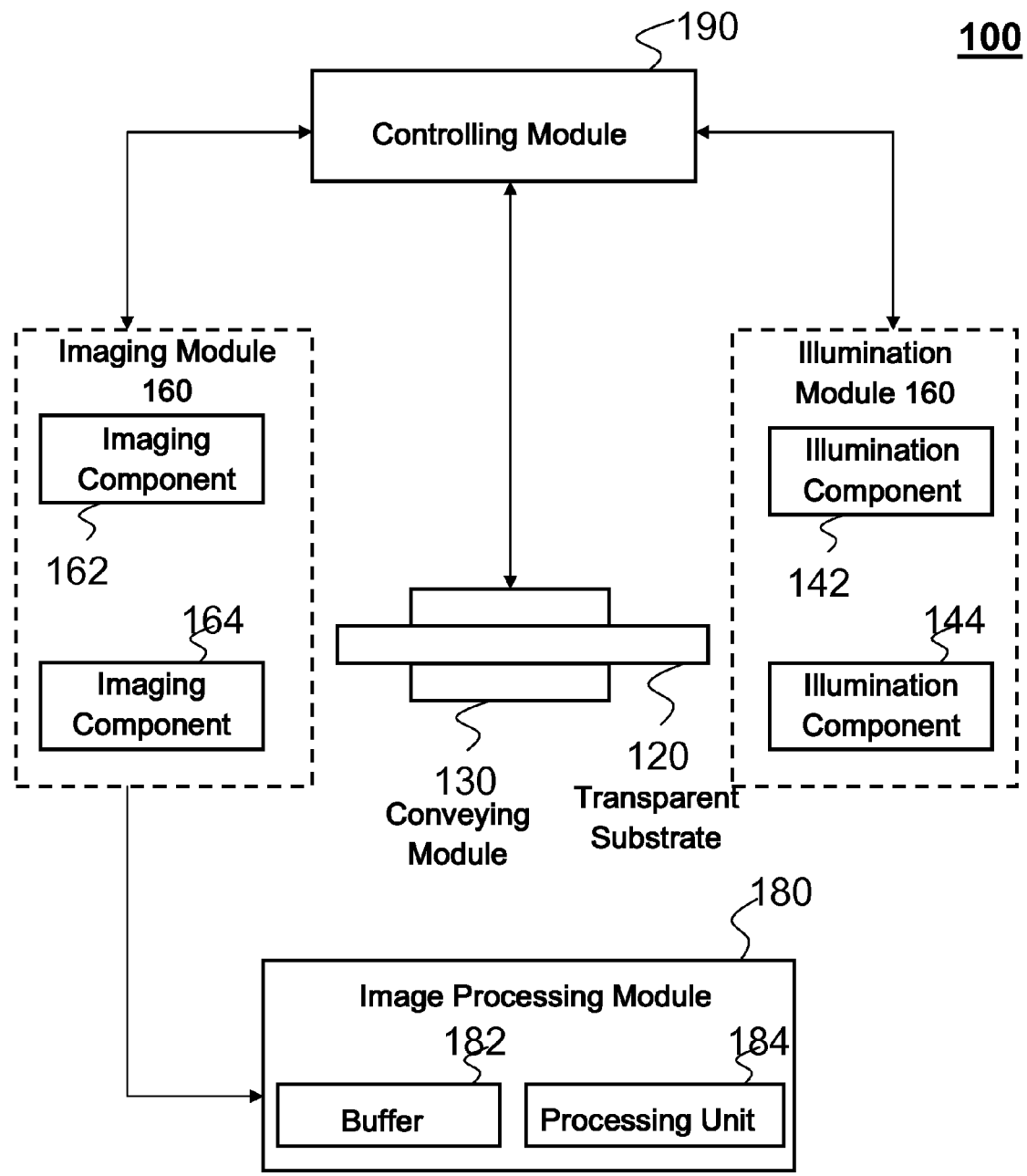
FIG. 1 is a schematic view illustrating a system for detecting defects of a transparent substrate according to a first embodiment of the present invention.

It is to be understood that the figures and descriptions of the present invention may have been simplified to illustrate elements that are relevant for a clear understanding of the present invention, while eliminating, for purposes of clarity, other elements found in a typical defect detection system. Those of ordinary skilled in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different from those shown in the drawings. Reference will now be made to the drawings wherein like structures are provided with like reference designations.

FIG. 1 shows a system 100 for detecting defects of a transparent substrate 120 according to a first embodiment of the present invention. The defect detection system 100 comprises a transport module 130, an illumination module 140, an imaging module 160, an image processing module 180 and a controlling module 190. In order to remove the influence of environment light, the whole system 100 may be covered with a black cover (not shown in FIG. 1).

In the first embodiment, the transparent substrate 120 may be glass, plastic, or any other transparent material, such as glass ribbon on float line, raw glass panel, glass substrate of photovoltaic module and glass substrate of flat panel display device. The substrate 120 is not limited to the form of a sheet having substantially parallel surfaces, but can be extended to the form of a cylinder curved in a plane vertical to transporting direction of the substrate. Unless otherwise specified, as used therein, the term "two opposite sides of the substrate" refers to two sides along a normal to surface of the substrate, i.e. two sides above and under the substrate 120 as illustrated in FIG. 2.

The transport module 130 is used to produce relative motion between the transparent substrate 120 and the imaging module 160 and the illumination module 140. For example, as indicated by arrow 132 in FIG. 2, relative motion may be developed by moving the substrate 120 relative to the imaging module 160 and the illumination module 140. Alternatively, relative motion may be developed by moving the illumination module 140 and the imaging module 160 relative to the substrate 120. For example, as substrates for use in display applications grow in size, moving the illumination module 140 and the imaging module 160 may become an attractive alternative to moving the substrate 120. The transport module 130 in the first embodiment may comprise, for example, a linear stage, stepper motors, conveyor belts, tracks, carriages, pneumatic tables, air bearings, or other conventional methods of conveying a substrate, camera and/or light sources. For purposes of illustration and not limitation, it will be hereinafter assumed that the illumination module 140 and the imaging module 160 keep to a fixed position and the substrate 120 is moved relative to the illumination module 140 and the imaging module 160. The transport module 130 preferably comprises an adjusting component for moving the substrate 120 in a direction of surface normal of the substrate 120, as indicated by Arrow 125 in FIG. 2, to maintain a consistent distance between the substrate 120 and the illumination module 140 and the imaging module 160. Further, the transport module 130 may also perform a flattening function to minimize errors due to flattering of the substrate 120 during scanning. Flattening may be performed in a conventional manner, such as using air pressure (e.g. air bearings).

Figure 2:
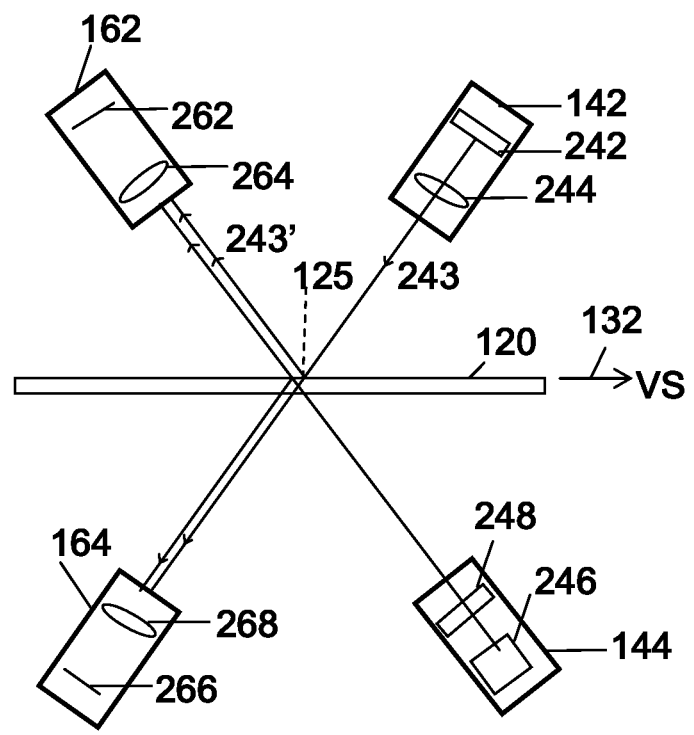
FIG. 2 is a schematic view illustrating a three-channel optical configuration according to the first embodiment of the present invention.

FIG. 2 illustrates the illumination module 140 and the imaging module 160 in the defect detection system 100 shown in FIG. 1 as well as position relationship between the two modules and the substrate 120. As illustrated in FIG. 2, in the defect detection system 100, the substrate 120 moves with a speed Vs in a direction indicated by Arrow 132 in FIG. 2. The imaging module 160 comprises a first imaging component 162 disposed above the transparent substrate 120 and a second imaging component 164 disposed under the transparent substrate 120. The first imaging component 162 comprises a first image sensor 262 and one or more imaging lenses, represented by imaging lens 264. Similarly, the second imaging component 164 comprises a second image sensor 266 and one or more imaging lenses, represented by imaging lens 268. the imaging lenses 264, 268 are used for collecting light and imaging the light onto the photosensitive planes of the first and second image sensors 262 and 266. As well know in the art, the imaging lenses comprise spherical lens, aspherical lens, microlens array or diffractive imaging elements. The imaging components 162 and 164 each has a numerical aperture defining the acceptance angle over which an imaging component is capable of receiving light, and is largely controlled by the imaging lens and any other aperture-limiting elements included in the imaging component, such as iris. The first and second image sensors 262 and 266 are used to sense light imaged on photosensitive planes thereof and converting the light into an electrical signal. In the first embodiment of the present invention, the first and second image sensors 262, 266 are line scanning camera, such as CCD line scanning sensor, CMOS line scanning sensor, or any other sensor type capable of converting light into an electrical signal. Line scanning cameras are readily commercially available and may be used to scan the substrate 120 one scan at a time at a rate of several hundred or even several hundred of hundreds scans per second. The first imaging component 162 and the second imaging component 164 have a pair of scanning lines which are substantially parallel on the substrate 120 and typically normal to the moving direction 132 of the substrate 120. The first and second imaging components 162 and 164 focus on the illuminated portion of the surface on the substrate 120. It is should be noted that, in practice, the focus lines on the surface of the substrate 120 of the two imaging components 162 and 164 do not necessarily coincide with each other strictly. The experiments demonstrate that parallel offset of less than 10 mm is acceptable. Note that a maximum of the offset may vary depending on configuration parameters of the whole detection system.

As illustrated in FIG. 2, in the first embodiment of the present invention, the illumination module 140 comprises two illumination components, a collimated illumination component 142 disposed above the transparent substrate 120 and a diffusive illumination component 144. The collimated illumination component 142 comprises a first light source 242 and a collimation optical element 244 (for example, one or more lenses). The light emitted by the first light source 242 becomes collimated light through the collimation optical element 244 and then impinges onto the substrate 120 in the direction indicated by Arrow 243. The collimated illumination component 142 is disposed such that the first light source 242 provides bright field illumination to the substrate 120 relative to the first imaging component 162. As shown in FIG. 2, the collimated illumination component 142 is located on the same side of the substrate 120 as the first imaging component 162 (they are both located above the substrate 120 in FIG. 2, but one skilled in the art should contemplate that they can be located under the substrate 120 correspondingly). At least a portion of light from the collimated illumination component 142 is reflected from the substrate 120 in a direction indicated by Arrow 243', and then sensed by the first imaging component 162, thereby providing a bright field illumination to the substrate 120 relative to the first imaging component 162 via a reflection path. Hereinafter, the bright field reflection detection channel constructed by the collimated illumination component 142 and the first imaging component 162 is also referred to a first detection channel or a first channel. Because of the fact that the collimated illumination mode is sensitive to deformation or inhomogeneousness in the substrate, the first detection channel can be used to detect knots, stones, and bubbles. In addition, tin pick-up defect on substrate 120 may be detected by use of specular reflection characteristic.

Turning again to FIG. 2, the diffusive illumination component 144 comprises a second light source 246 and a diffuser 248 placed between the second light source 246 and the substrate 120. Light emitted by the second light source 246 becomes diffusive light through the diffuser 248, thereby illuminating the substrate 120 in a diffusive illumination mode. The diffusive illumination component 144 is disposed such that it provides bright field illumination to the substantially same portion of the substrate 120 as illuminated by the collimated illumination component 142 relative to the first and second imaging components 162 and 164. As shown in FIG. 2, the diffusive illumination component 144 is located on the same side of the substrate 120 as the second imaging component 164 (they are both located under the substrate 120 in FIG. 2, but one skilled in the art should contemplate that they can be located above the substrate 120 correspondingly). The illumination components 142 and 144 have normal lines nearly symmetrical as to the plane where the substrate is located.

At least a portion of light projected on the substrate 120 from the diffusive illumination component 144 is transmitted through the substrate 120 and sensed by the first imaging component 162, thereby providing bright field illumination to the substrate 120 relative to the first imaging component 162 via a transmission path. Hereinafter, the bright field transmission detection channel constructed by the diffusive illumination component 144 and the first imaging component 162 is also referred to a second detection channel or a second channel. The second detection channel can be used to detect core size and shape of the defects.

Meanwhile, substantially remaining portion of light projected on the substrate 120 from the diffusive illumination component 144 is reflected from the substrate 120 and sensed by the second imaging component 164, thereby providing bright field illumination to the substrate 120 relative to the second imaging component 164 via a reflection path. Hereinafter, the bright field reflection detection channel constructed by the diffusive illumination component 144 and the second imaging component 164 is also referred to a third detection channel or a third channel. The third detection channel can be used to determine depths of the defects in the substrate.

It should be noted that, in the first embodiment of the present invention, the first and second light sources 242 and 246 may be semiconductor light sources, such as light emit diode (LED) or laser diode (LD). Further, in the first embodiment of the present invention, light sources may be of any spectral range as long as the first and second image sensors may be photosensitive to light emitted by the light sources. Further, in the first embodiment of the present invention, light sources are not limited to monochromatic ones. Polychromatic light source having a wide spectral range is possible, such as a white light source.

Referring back to FIG. 1, the imaging module 160 sends a plurality of sensed images to the image processing module 180 which in turn perform image storing, image pre-processing, features extraction, images combination or the like. As shown in FIG. 1, the image processing module 180 preferably comprises a data buffer 182 (memory 182) and a processing unit (e.g. central processing unit) 184 for processing data from the imaging module 160.

In the first embodiment of the present invention, the two illumination components, i.e., the collimated illumination component 142 and the diffusive illumination component 144, are not switched on simultaneously, but used to illuminate the substrate 120 alternately. The first imaging component 162 works either when the collimated illumination component 142 switches on or when the diffusive illumination component 144 switches on. While the second imaging component 164 works only when the diffusive illumination component 142 switches on. Therefore, the operation of the defect detection system 100 may proceed in the following manner. As the substrate 120 is moved past the illumination module 140 and the imaging module 160, the first light source 242 of the collimated illumination component 142 is switched on, while the first imaging component 162 begins to capture light reflected from the substrate 120, thereby performing the first channel detection. Then, the first light source 242 of the collimated illumination component 142 is switched off, and the second light source 246 of the diffusive illumination component 144 is switched on while the first imaging component 162 and the second imaging component 164 begins to capture light transmitting through he substrate 120 and reflected from the substrate 120, respectively, thereby performing the second channel detection and the third channel detection simultaneously. It is apparently possible to one skilled in the art that the second and third channel detections are performed first and then the first channel detection is performed.

The defect detection system 100 in FIG. 1 is provided with a controlling module 190 which is used to control work timing of the illumination components 142, 144 and the imaging components 162, 164 as described above. Now the controlling module 190 of the defect detection system 100 of the first embodiment of the present invention is described in detail referring to FIG. 3. The controlling module 190 acts as an external trigger for controlling trigger timing of each of the illumination components and the imaging components. The controlling module 190 may be any type of pulse trigger, such as but not limited to an encoder.

Specifically, the controlling module 190 is used to sense displacement of the substrate 120 and control all of the channel detections to be completed within every working period, the working period means a period over which the substrate 120 moves a certain displacement $$\Delta L = \frac{P}{M},$$

where P denotes pixel width of the image sensor in the imaging component, and M denotes imaging magnification of the image sensor. The controlling module 190 then divides one working period into n equal or unequal parts based on number of groups n (n is a positive integral which is 2 or more) of the detection channels which do not work simultaneously, resulting in trigger pulse sequence $T_i$ (i is a positive integral) shown in FIG. 3. Specifically, in the three-channel configuration of the present embodiment, since the first channel detection and then the second and third channel detections are performed in one working period $\Delta T$, one working period $\Delta T$ comprises two trigger pulses, such as $T_1$ and $T_2$, i.e. n=2. The controlling module 190 also controls operations of each of the imaging components so as to scan the illuminated substrate when illumination from the light source is stable. It is noted that durations of n pulses included in one working period may be equal or unequal. For example, in order to improve signal-to-noise ratio of data obtained from reflection channels, the duration of the reflection channel may be set to be longer than that of the transmission channel.

Figure 3:
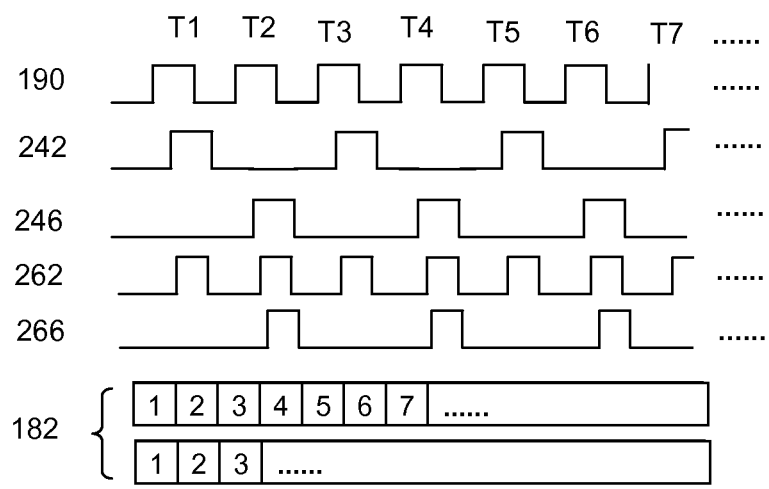
FIG. 3 is a time chart showing trigger timings of each of components in the three-channel optical configuration according to the first embodiment of the present invention.

Now controlling operation of the controlling module 190 with respect to each of the light sources and the imaging components is described referring to trigger pulse sequences shown in FIG. 3. During $T_1$ pulse period, after a certain delay of leading edge of pulse 1 generated by the controlling module 190, the first light source 242 switches on and illuminates the substrate 120 for a certain pulse width (which is less than a pulse period). The first image sensor 262 of the first imaging component 162 begins to sense the light after the first light source 242 switches on. The first light source 242 then switches off before leading edge of pulse 2 comes while the first image sensor 262 is controlled to stop sensing. During period of the first light source 242 being on, the second light source 246 keeps in off status while the second image sensor 266 is in a state of not sensing the light, and the first imaging component 162 captures light reflected from the substrate 120 and sends obtained data to the image processing module 180. The imaging processing module 180 then stores received data in an array for the first imaging component 162 in the buffer 182.

After a certain delay of leading edge of pulse 2, the second light source 246 switches on and illuminates the substrate 120 for a certain pulse width. The first image sensor 262 and the second image sensor 266 begins to sense the light after the second light source 246 switches on. The second light source 246 then switches off before leading edge of pulse 3 comes while the first image sensor 262 and the second image sensor 266 are controlled to stop sensing. During period of the second light source 246 being on, the first light source 242 keeps off, while the first imaging component 162 and the second imaging component 164 capture light transmitting through the substrate 120 and reflected from the substrate 120, respectively, and send obtained data to the image processing module 180. The imaging processing module 180 then stores data received from the first imaging component 162 and the second imaging component 164 in arrays for both of the imaging components in the buffer 182, respectively.

Similarly, during odd-numbered pulse period $T_{2j-1}$ (j is a positive integral), the first light source 242 and the first image sensor 262 work, and data obtained from the first imaging component 162 is stored in the buffer 182; while during even-numbered pulse period $T_{2j}$ (j is a positive integral), the second light source 246 works together with the first and second image sensors 262 and 266, and data obtained from the first and second imaging components 162 and 164 are stored in the buffer 182.

FIG. 4 shows raw images obtained by the above three-channel configuration of the first embodiment of the present invention. FIG. 4A shows raw image obtained by the first image sensor 262 of the first imaging component 162, the raw image containing data from two channels, the first channel and the second channel. Raw image shown in FIG. 4A looks like pattern of grating with alternate bright lines and dark lines, where dark lines represent data obtained from the first channel during odd-numbered pulse period $T_{2j-1}$ while bright lines represent data obtained from the second channel during even-numbered pulse period $T_{2j}$ since the first channel is bright field reflection channel while the second channel is bright field transmission channel. FIG. 4B shows raw image obtained by the second image sensor 266 of the second imaging component 164. Since the raw image in FIG. 4B only represents data obtained from the third channel during even-numbered pulse period T2*j*, the image is of ½ size of that shown in FIG. 4A.

Figure 4A:
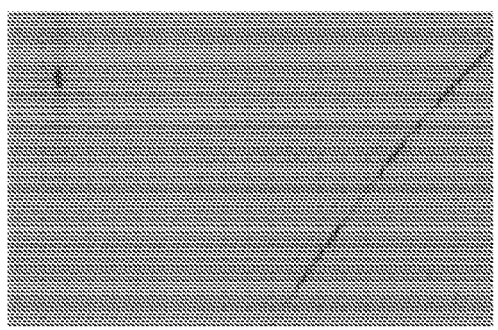
FIG. 4 is a view showing raw images obtained by the three-channel detection system according to the first embodiment of the present invention.

Then, the image shown in FIG. 4A is separated and recombined. Specifically, data obtained from the first channel during odd-numbered pulse period $T_{2j-1}$ are extracted and recombined into an image shown in FIG. 4C; remaining data obtained from the second channel during even-numbered pulse period $T_{2j}$ recombined into an image shown in FIG. 4D. Thus, three images of same sizes are obtained, that is, image representing data from the first channel shown in FIG. 4C, image representing data from the second channel shown in FIG. 4D and image representing data from the third channel shown in FIG. 4B. The processing unit 184 of the image processing module 180 performs feature extraction on the obtained three images to identify and categorize defects of the substrate 120. Such feature extraction for example includes analysis on the defect profile, variation of grayscale, mean value of grayscale and the like features of defects and calculations of core size, deformation size and other key parameters for defect classification. Furthermore, by processing data obtained from a multiple of channels, it may be accurately judged whether a defect is located on top surface, bottom surface or inside the substrate, even to determine depth of an internal defect.

Figure 4C:
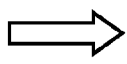
Figure 4C:
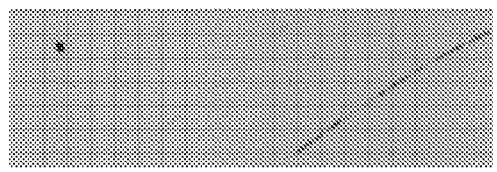
Figure 4D:
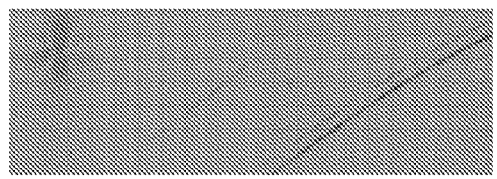
Figure 4B:

It should be noted that, in the present embodiment, data are stored for each of the imaging components in the buffer 182 of the image processing module 180. Apparently, when high real-time detection performance is required, for example when on-line detection is performed, data may be stored for each of the detection channels in the buffer 182. In such cases, image for each of the detection channels as shown in FIGS. 4C and 4D may be directly obtained without need of above separation and recombination operations.

It is demonstrated experimentally that the defect detection system 100 of the present embodiment is capable of accurately identify and categorize various defects such as bubbles, stones, scratches, chips, tin pick-ups, knots. Compared to the defect detection system of the prior art, the defect detection system 100 shown in FIG. 2 is compact and small-size. Furthermore, since the illumination light sources work in a pulse mode which facilitates heat dissipation, light sources may have a long lifetime and provide higher brightness. Further, it is also demonstrated experimentally that by analyzing integrated data obtained from multiple channels with inter-channel interference being eliminated, effects of dust on the substrate surface on defects detection and categorization are significantly weakened. Therefore, by the above configuration of the present embodiment, it is unnecessary to clean the substrate before detection, thereby saving the expenses for cleaning device and operations thereof while satisfying requirements for no cleaning of substrate in some certain applications.

One skilled in the art will recognize that the present invention is not limited to the disclosed precise forms and may variations and changes are apparent. For example, in the defect detection system of the present embodiment, the number of detection channels is not limited to three and the number of imaging components is not limited to two, and more than two light sources may be used. Moreover, in case of the substrate having larger size, a plurality of groups of imaging components may be used, each group comprising one or more imaging components and constructing a certain mode of detection channel together with light sources.

Figure 5A:
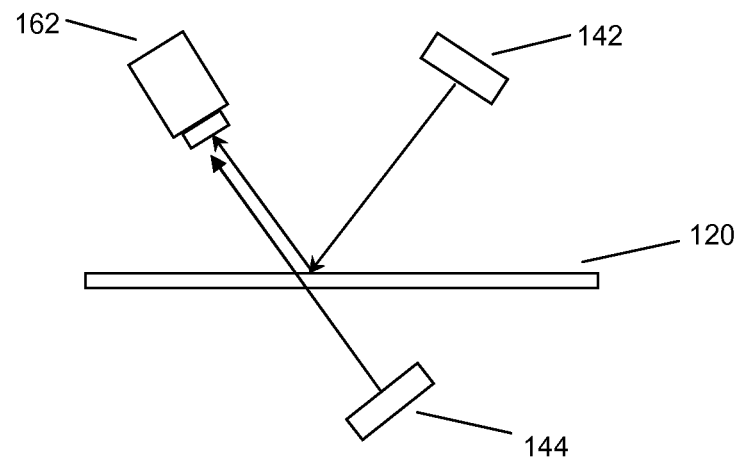
FIG. 5 is a schematic view illustrating two-channel optical configurations according to a second embodiment of the present invention.
Figure 5B:
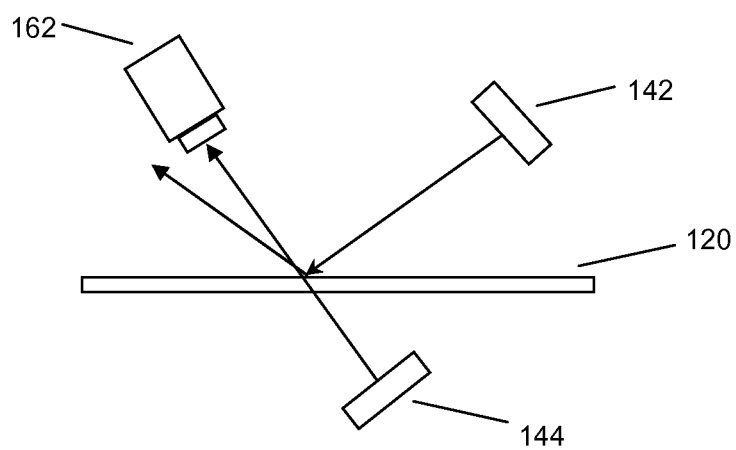

For example, a modification of the first embodiment of the present invention may use a four-channel optical configuration which is similar to three-channel optical configuration shown in FIG. 2 except that the collimated illumination component 142 in FIG. 2 is replaced by a diffusive illumination component 642. The controlling module 190 controls such that each of the first imaging component 162 and the second imaging component 164 captures images when any one of the diffusive illumination components 642 and 142 switches on, thereby constructing two reflection detection channels and two transmission detection channels with respect to the substrate 120. In addition, the second embodiment of the present invention may use two-channel optical configuration shown in FIG. 5A and FIG. 5B where only the imaging component 162 is used and the second imaging component 164 is omitted compared to the three-channel optical configuration shown in FIG. 2. In the two-channel optical configuration shown in FIG. 5A, the first light source 142 and the imaging component 162 construct a first channel which is of bright field reflection mode, while the second light source 144 and the imaging component 162 construct a second channel which is of bright field transmission mode. The controlling module 190 controls the two light sources 142 and 144 to switch on alternately by trigger pulse, and controls the imaging component 162 so as to work when each of the light sources 142 and 144 switches on, thereby obtaining data from the first channel and the second channel. Data from the first channel may be used to detect defects such as tin pick-up, stones, bubbles and knots of the substrate 120, and depth of the defects may be determined based on ghost images from the reflection channel. Data from the second channel may be used to determine shape and size of the defects of the substrate 120. In another two-channel configuration shown in FIG. 5B, the first light source 142 and the imaging component 162 construct the first channel which is of dark field reflection mode, while the second light source 144 and the imaging component 162 construct the second channel which is of bright field transmission channel. Similarly, the controlling module 190 controls the two light sources 142 and 144 to switch on alternately by trigger pulse, and controls the imaging component 162 so as to work when each of the light sources 142 and 144 switches on, thereby obtaining data from the detection channels of different modes to detect various type of defects on or in the substrate.

Figure 6:
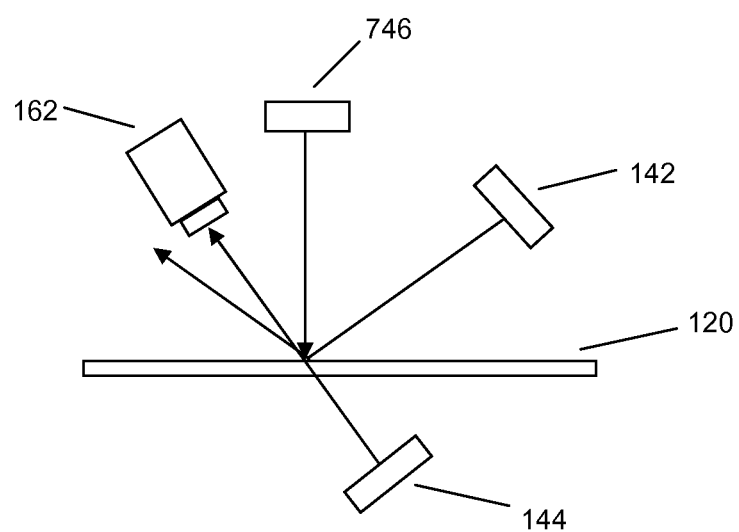
FIG. 6 is a schematic view illustrating multi-light source optical configuration according to a third embodiment of the present invention.

In addition, for example, the detection system of the third embodiment of the present invention may use one imaging component 162 and a plurality of (three in the embodiment shown in FIG. 6) illumination components 142, 144, 746. As illustrated in FIG. 6, the illumination components 142 and 746 are located on the same side of the substrate 120 as the imaging component 162, while the illumination component 144 is located on the other side of the substrate 120. Here, the illumination components 142 and 746 provide dark field reflection illumination to the substrate 120 relative to imaging component 162 at different illumination angles, while the illumination component 144 provides bright field transmission illumination to the substrate 120 relative to imaging component 162. The controlling module 190 performs controlling operation so that the illumination component 142 and illumination component 746 may switch on simultaneously or not simultaneously, but either of them is switched on simultaneously with the illumination component 144. The controlling module 190 also controls such that the imaging component 162 scans the substrate 120 when the substrate 120 is illuminated.

Figure 7:
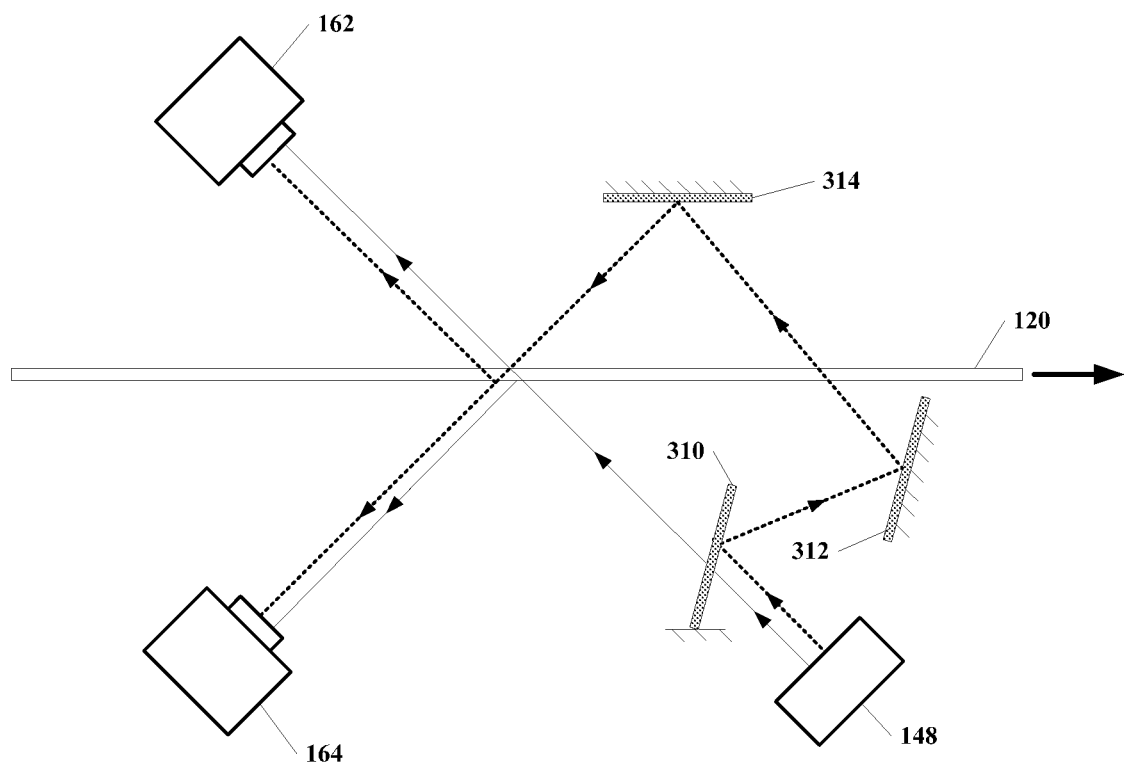
FIG. 7 is a schematic view illustrating a four-channel optical configuration according to a fourth embodiment of the present invention.

FIG. 7 illustrates a four-channel optical configuration according to a fourth embodiment of the present invention. As shown in FIG. 7, the system 100 includes four detection channels, i.e., a first detection channel, a second detection channel, a third detection channel and a fourth detection channel.

The first detection channel may include a dichromic mirror 310 placed on one side of the substrate 120 and capable of transmitting a red color light to the substrate 120 and reflecting a blue color light, a dual color illumination component 148 placed on the one side of the substrate 120 and capable of emitting the red color light and the blue color light, and the first imaging component 162 placed on another opposite side of the substrate 120. The dual color illumination component 148 may be a dual color LED. In the first detection channel, the dual color illumination component 148 may emit the red color light to the dichromic mirror 310, the dichromic mirror 310 may transmit through the red color light received from the dual color illumination component 148 to the substrate 120, and the first imaging component 162 scans the substrate 120 to provide an image of the substrate 120 by sensing the red color light that is from the dichromic mirror 310 and transmits through the substrate 120. That is, in the first detection channel, the dual color illumination component 148 provides bright field transmission illumination to the substrate 120 with respect to the first imaging component 162 via the dichromic mirror 310.

The second detection channel may include the dichromic mirror 310, the dual color illumination component 148 and the second imaging component 164 placed on the one side of the substrate 120. In the second detection channel, the dual color illumination component 148 may emit the red color light to the dichromic mirror 310, the dichromic mirror 310 may transmit through the red color light received from the dual color illumination component 148 to the substrate 120, and the first imaging component 162 scans the substrate 120 to provide an image of the substrate 120 by sensing the red color light that is from the dichromic mirror 310 and is reflected by the substrate 120. That is, in the second detection channel, the dual color illumination component 148 provides bright field reflection illumination to the substrate 120 with respect to the second imaging component 164 via the dichromic mirror 310.

The third detection channel may include the dichromic mirror 310, the dual color illumination component 148, the first imaging component 162, a reflection mirror 312 placed on the one side of the substrate 120 and a reflection diffuser 314 placed on the another opposite side of the substrate 120. In the third detection channel, the dual color illumination component 148 may emit the blue color light to the dichromic mirror 310, the dichromic mirror 310 may reflect the blue color light received from the dual color illumination component 148, the reflection mirror 312 may receive the blue color light reflected by the dichromic mirror 310 and reflect the received blue color light, the reflection diffuser 314 may receive the blue color light reflected by the reflection mirror 312, form a diffusive blue color light and emit the diffusive blue color light to the substrate 120, and the first imaging component 162 scans the substrate 120 to provide an image of the substrate 120 by sensing the blue color light that is from the reflection diffuser 314 and is reflected by the substrate 120. That is, in the third detection channel, the dual color illumination component 148 provides bright field reflection illumination to the substrate 120 with respect to the first imaging component 162 via the dichromic mirror 310, the reflection mirror 312 and the reflection diffuser 314.

The fourth detection channel may include the dichromic mirror 310, the dual color illumination component 148, the second imaging component 164, the reflection mirror 312 and the reflection diffuser 314. In the fourth detection channel, the dual color illumination component 148 may emit the blue color light to the dichromic mirror 310, the dichromic mirror 310 may reflect the blue color light received from the dual color illumination component 148, the reflection mirror 312 may receive the blue color light reflected by the dichromic mirror 310 and reflect the received blue color light, the reflection diffuser 314 may receive the blue color light reflected by the reflection mirror 312, form a diffusive blue color light and emit the diffusive blue color light to the substrate 120, and the second imaging component 164 scans the substrate 120 to provide an image of the substrate 120 by sensing the blue color light that is from the reflection diffuser 314 and transmits through the substrate 120. That is, in the fourth detection channel, the dual color illumination component 148 provides bright field transmission illumination to the substrate 120 with respect to the second imaging component 164 via the dichromic mirror 310, the reflection mirror 312 and the reflection diffuser 314.

The dual color illumination component 148 may a diffusive illumination component or a collimated illumination component, and may work in pulse mode.

The first imaging component 162 and the second imaging component 164 may scan the substantially same zone of the substrate 120 to provide images of the substrate 120.

Figure 8:
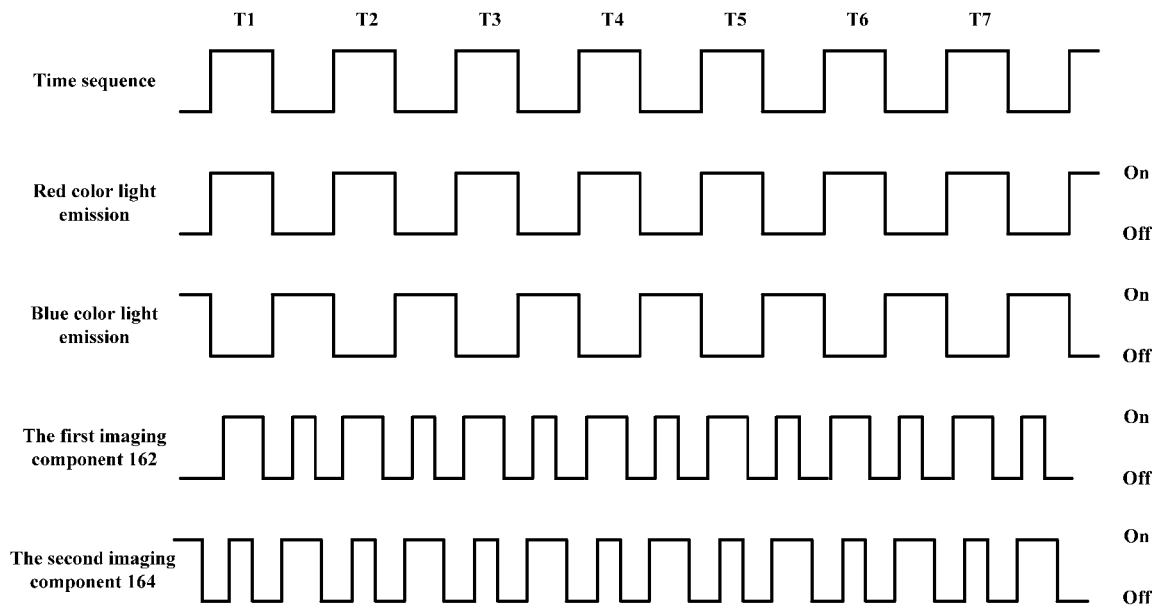
FIG. 8 is a time chart showing trigger timings of each of components in the four-channel optical configuration according to the fourth embodiment of the present invention.

FIG. 8 is a time chart showing work timing of the dual color illumination component, the first imaging component and the second imaging component in the four-channel optical configuration according to the fourth embodiment of the present invention.

As shown in FIG. 8, the controlling module 190 may control the dual color illumination component 148 to emit the red color light and the blue color light alternately, and control the first imaging component 162 and the second imaging component 164 to scan the substrate 120 at the same time when the dual color illumination component 148 emits the red color light and the blue color light. Scanning duration (exposure time) of the first imaging component 162 when the illumination component included in the same detection channel as the first imaging component 162 provides reflection illumination to the substrate is larger than that of the first imaging component 162 when the illumination component included in the same detection channel as the first imaging component 162 provides transmission illumination to the substrate and that of the second imaging component 164 when the illumination component included in the same detection channel as the second imaging component 164 provides transmission illumination to the substrate, and scanning duration (exposure time) of the second imaging component 164 when the illumination component included in the same detection channel as the second imaging component 164 provides reflection illumination to the substrate is larger than that of the second imaging component 164 when the illumination component included in the same detection channel as the second imaging component 164 provides transmission illumination to the substrate and that of the first imaging component 162 when the illumination component included in the same detection channel as the first imaging component 162 provides transmission illumination to the substrate.

Those skilled in the art will understand that in the above fourth embodiment, the first, second, third and fourth detection channels use the dual color illumination component 148 capable of emitting the red color light and the blue color light to provide the illumination, but the present invention is not so limited.

In some other embodiments of the present invention, the first and second detection channels may use a first illumination component capable of emitting the red color light to provide the illumination, the third and fourth detection channels may use a second illumination component capable of emitting the blue color light to provide the illumination, and the first illumination component and the second illumination component are placed on the same position as the dual color illumination component 148. The controlling module 190 may control the first illumination component and the second illumination component to emit the light to the dichromic mirror 310 alternately, and control the first imaging component 162 and the second imaging component 164 to scan the substrate 120 at the same time when the first illumination component and the second illumination component emit the light.

Those skilled in the art will understand that in the above fourth embodiment, the red color light and the blue color light are used as a first color light and a second color light to provide the illumination, but the present invention is not so limited. In some other embodiments of the present invention, the first color light may be other color light except for the red color light and the second color light may be other color light except for the blue color light.

Those skilled in the art will understand that in the above fourth embodiment, the exposure time of the first imaging component 162 when the illumination component included in the same detection channel as the first imaging component 162 provides reflection illumination to the substrate is larger than that of the first imaging component 162 when the illumination component included in the same detection channel as the first imaging component 162 provides transmission illumination to the substrate and that of the second imaging component 164 when the illumination component included in the same detection channel as the second imaging component 164 provides transmission illumination to the substrate, and the exposure time of the second imaging component 164 when the illumination component included in the same detection channel as the second imaging component 164 provides reflection illumination to the substrate is larger than that of the second imaging component 164 when the illumination component included in the same detection channel as the second imaging component 164 provides transmission illumination to the substrate and that of the first imaging component 162 when the illumination component included in the same detection channel as the first imaging component 162 provides transmission illumination to the substrate.

In some other embodiments of the present invention, the exposure time of the first imaging component 162 when the illumination component included in the same detection channel as the first imaging component 162 provides reflection illumination to the substrate may also be equal to or shorter than that of the first imaging component 162 when the illumination component included in the same detection channel as the first imaging component 162 provides transmission illumination to the substrate and that of the second imaging component 164 when the illumination component included in the same detection channel as the second imaging component 164 provides transmission illumination to the substrate, and the exposure time of the second imaging component 164 when the illumination component included in the same detection channel as the second imaging component 164 provides reflection illumination to the substrate may also be equal to or shorter than that of the second imaging component 164 when the illumination component included in the same detection channel as the second imaging component 164 provides transmission illumination to the substrate and that of the first imaging component 162 when the illumination component included in the same detection channel as the first imaging component 162 provides transmission illumination to the substrate.

Those skilled in the art will understand that in the first, second, third and fourth embodiment, the illumination components provide bright field illumination to the substrate, but the present invention is not so limited. In some other embodiments of the present invention, the illumination components may also provide dark field illumination to the substrate.

The foregoing description of all aspects of the present invention is given for the purpose of illustration and explanation. It is not intend to exhaustively describe or limit the present invention to the disclosed precise forms, while many variations and changes are apparent. Therefore, it should be comprehended that the present invention is not limited to the disclosed specific embodiments but is intended to cover all possible modifications and variations defined by the appending claims.

What is claimed is:

1. A system for detecting defects of a transparent substrate, comprising:
    a plurality of detection channels, each of which includes an illumination component for providing illumination to the substrate and an imaging component for scanning the substrate to provide image of the substrate;
    a transport module, for producing relative motion between the substrate and the illumination components and the imaging components included in the plurality of detection channels; and
    a controlling module, for controlling the illumination components and the imaging components included in the plurality of detection channels so that at least two illumination components of the illumination components included in the plurality of detection channels provide illumination to the substrate alternately, and the imaging component included in any of the plurality of detection channels scans the substrate when the illumination component included in that detection channel illuminates the substrate,
    wherein the imaging components included in at least two detection channels of the plurality of detections channels are the same imaging component,
    wherein, at least two of the illumination components included in the plurality of detection channels are one and the same illumination component so that said same illumination component is shared by two different detection channels of said plurality of detection channels,
    wherein the plurality of detection channels includes a first detection channel, a second detection channel, a third detection channel and a fourth detection channel,
    wherein the illumination component and the imaging component included in the first detection channel are placed on one side of the substrate, and the illumination component included in the first detection channel provides reflection illumination to the substrate with respect to the imaging component included in the first detection channel,
    wherein the imaging component included in the second detection channel is placed on another opposite side of the substrate and the illumination component included in the second detection channel is placed on the one side of the substrate, and the illumination component included in the second detection channel provides transmission illumination to the substrate with respect to the imaging component included in the second detection channel, wherein the imaging component included in the third detection channel is placed on the one side of the substrate and the illumination component included in the third detection channel is placed on the another opposite side of the substrate, and the illumination component included in the third detection channel provides transmission illumination to the substrate with respect to the imaging component included in the third detection channel, wherein the illumination component and the imaging component included in the fourth detection channel are placed on the another opposite side of the substrate, and the illumination component included in the fourth detection channel provide reflection illumination to the substrate with respect to the imaging component included in the fourth detection channel, wherein the imaging components included in the first and third detection channels are one and the same first imaging component and the imaging components included in the second and fourth detection channels are one and the same second imaging component, wherein the illumination components included in the first and second detection channels are one and the same first illumination component and the illumination components included in the third and fourth detection channels are one and the same second illumination component, and wherein the controlling module controls the first and second illumination components to illuminate the substrate alternately, and controls the first imaging component and the second imaging component to scan the substrate at the same time when the first illumination component and the second illumination components illuminate the substrate.

2. The system according to claim 1, wherein
the plurality of detection channels includes at least two of the first detection channels and
the imaging components included in the at least two of the first detection channels are one and the same first imaging component.

3. The system according to claim 1, further comprising:
an image processing module, for performing image processing on the image of the substrate from each of the plurality of detection channels, to detect defects of the substrate.

4. The system according to claim 1, wherein
the imaging components included in the plurality of detection channels scan the substantially same zone of the substrate to provide images of the substrate.

5. The system according to claim 1, wherein
the illumination components included in the plurality of detection channels work in pulse mode.

6. The system according to claim 1, wherein
the controlling module controls illumination time of each of the illumination components included in the plurality of detection channels and exposure time of each of the imaging components included in the plurality of detection channels so that each of the plurality of detection channels completes scanning of the substrate one time within a working period, the working period being defined as time duration when the substrate moves a certain displacement P/M, where P denotes pixel size of the illumination components, and M denotes imaging magnification of the imaging components.

7. The system according to claim 1, wherein
the controlling module controls the imaging components included in the plurality of detection channels so that exposure time of a first imaging component of the imaging components when the illumination component included in the same detection channel as the first imaging component provides reflection illumination to the substrate is different from that of a second imaging component of the imaging components when the illumination component included in the same detection channel as the second imaging component provides transmission illumination to the substrate.

8. The system according claim 1, wherein
each of the illumination components included in the plurality of detection channels are a diffusive illumination component or a collimated illumination component.

9. The system according to claim 1, wherein
each of the illumination components included in the plurality of detection channels includes a semiconductor light source.

10. The system according to claim 9, wherein
the semiconductor light source is a light emitting diode or a laser diode.

11. The system according to claim 9, wherein
the semiconductor light source is a monochromatic light source or a polychromatic light source.

12. The system according to claim 1, wherein
each of the imaging components included in the plurality of detection channels comprises at least one imaging lens and a line scan photo-detector.

13. The system according to claim 12, wherein
the at least one imaging lens is selected from a group comprising spherical lenses, aspherical lenses, micro-lens arrays or diffractive imaging elements.

14. The system according to claim 12, wherein
the line scan photo-detector includes line scan CCD sensor or line scan CMOS sensor.

15. The system according to claim 12, wherein
the substrate includes float glass ribbon, raw glass panel, glass substrate of photovoltaic module and glass substrate of flat panel display device.

16. The system according to claim 12, wherein
the system is capable of detecting and categorizing defects of the substrate, wherein the defects include scratches, stains, tin pick-ups, chips, bubbles, black stones, white stones, and knots.

17. The system according to claim 16, wherein
the system is capable of discriminating internal defects and surface defects and further determining depth of the defects of the substrate.

18. The system according to claim 16, wherein
the system is capable of detecting and categorizing the defects of the substrate even with presence of foreign particles on the substrate.

19. The system according to claim 18, wherein
the substrate is not cleaned.

20. A method for detecting defects of a transparent substrate, comprising:
using a plurality of detection channels to provide images of the substrate, wherein each of the plurality of detection channels includes an illumination component for providing illumination to the substrate and an imaging component for scanning the substrate to provide an image of the substrate;
producing relative motion between the substrate and the illumination components and the imaging components included in the plurality of detection channels; and
controlling the illumination components and the imaging components included in the plurality of detection channels so that all or parts of the illumination components included in the plurality of detection channels provide illumination to the substrate alternately, and the imaging component included in any of the plurality of detection channels scans the substrate when the illumination component included in that detection channel illuminates the substrate, wherein the imaging components included in at least two detection channels of the plurality of detections channels are the same imaging component, wherein at least two of the illumination components included in the plurality of detection channels are one and the same illumination component so that said same illumination component is shared by two different detection channels of said plurality of detection channels, wherein the plurality of detection channels includes a first detection channel, a second detection channel, a third detection channel and a fourth detection channel, wherein the illumination component and the imaging component included in the first detection channel are placed on one side of the substrate, and the illumination component included in the first detection channel provides reflection illumination to the substrate with respect to the imaging component included in the first detection channel, wherein the imaging component included in the second detection channel is placed on another opposite side of the substrate and the illumination component included in the second detection channel is placed on the one side of the substrate, and the illumination component included in the second detection channel provides transmission illumination to the substrate with respect to the imaging component included in the second detection channel, wherein the imaging component included in the third detection channel is placed on the one side of the substrate and the illumination component included in the third detection channel is placed on the another opposite side of the substrate, and the illumination component included in the third detection channel provides transmission illumination to the substrate with respect to the imaging component included in the third detection channel, wherein the illumination component and the imaging component included in the fourth detection channel are placed on the another opposite side of the substrate, and the illumination component included in the fourth detection channel provide reflection illumination to the substrate with respect to the imaging component included in the fourth detection channel, wherein the imaging components included in the first and third detection channels are one and the same first imaging component and the imaging components included in the second and fourth detection channels are one and the same second imaging component, wherein the illumination components included in the first and second detection channels are one and the same first illumination component and the illumination components included in the third and fourth detection channels are one and the same second illumination component, and wherein the controlling step further comprises controlling the first and second illumination components to illuminate the substrate alternately, and controlling the first imaging component and the second imaging component to scan the substrate at the same time when the first illumination component and the second illumination components illuminate the substrate.

21. The method according to claim 20, wherein
the plurality of detection channels includes at least two of the first detection channels and
the imaging components included in the at least two of the first detection channels are one and the same first imaging component.

22. The method according to claim 20, further comprising:
performing image processing on the image of the substrate from each of the plurality of detection channels, to detect defects of the substrate.

23. The method according to claim 20, wherein
the imaging components included in the plurality of detection channels scan the substantially same zone of the substrate to provide images of the substrate.

24. The method according to claim 20, wherein
the illumination components included in the plurality of detection channels work in pulse mode.

25. The method according to claim 20, wherein
the controlling step further comprising controlling illumination time of each of the illumination components included in the plurality of detection channels and exposure time of each of the imaging components included in the plurality of detection channels so that each of the plurality of detection channels completes scanning of the substrate one time within a working period, the working period being defined as time duration when the substrate moves a certain displacement P/M, where P denotes pixel size of the illumination components, and M denotes imaging magnification of the imaging components.

26. The method according to claim 20, wherein
the controlling step further comprising controlling the imaging components included in the plurality of detection channels so that exposure time of a first imaging component of the imaging components when the illumination component included in the same detection channel as the first imaging component provides reflection illumination to the substrate is different from that of a second imaging component of the imaging components when the illumination component included in the same detection channel as the second imaging component provides transmission illumination to the substrate.

27. The method according to claim 20, wherein
each of the illumination components included in the plurality of detection channels is a diffusive illumination component or a collimated illumination component.

28. The method according to claim 20, wherein
each of the illumination components included in the plurality of detection channels includes a semiconductor light source.

29. The method according to claim 28, wherein
the semiconductor light source is a light emitting diode or a laser diode.

30. The method according to claim 28, wherein
the semiconductor light source is a monochromatic light source or a polychromatic light source.

31. The method according to claim 20, wherein
each of the imaging components included in the plurality of detection channels comprises at least one imaging lens and a line scan photo-detector.

32. The method according to claim 31, wherein
the at least one imaging lens is selected from a group comprising spherical lenses, aspherical lenses, micro-lens arrays or diffractive imaging elements.

33. The method according to claim 31, wherein the line scan photo-detector includes line scan CCD sensor or line scan CMOS sensor.

34. The method according to claim 31, wherein the substrate includes float glass ribbon, raw glass panel, glass substrate of photovoltaic module and glass substrate of flat panel display device.

35. The method according to claim 31, wherein the method is capable of detecting and categorizing defects of the substrate, wherein the defects include scratches, stains, tin pick-ups, chips, bubbles, black stones, white stones, and knots.

36. The method according to claim 35, wherein the method is capable of discriminating internal defects and surface defects and further determining depth of the defects of the substrate.

37. The method according to claim 36, wherein the method is capable of detecting and categorizing the defects of the substrate even with presence of foreign particles on the substrate.

38. The method according to claim 36, wherein the substrate is not cleaned.

* * * * *